United States Patent
DiMeo

(10) Patent No.: US 10,519,498 B2
(45) Date of Patent: Dec. 31, 2019

(54) ADDITIVES TO IMPROVE SEQUENCING BY SYNTHESIS PERFORMANCE

(71) Applicant: QIAGEN Waltham, Inc., Waltham, MA (US)

(72) Inventor: James J. DiMeo, Needham, MA (US)

(73) Assignee: Qiagen Sciences, LLC, Germantown, MD (US)

( * ) Notice: Subject to any disclaimer, the term of this patent is extended or adjusted under 35 U.S.C. 154(b) by 127 days.

(21) Appl. No.: 15/427,718

(22) Filed: Feb. 8, 2017

(65) Prior Publication Data

US 2017/0233805 A1    Aug. 17, 2017

Related U.S. Application Data

(60) Provisional application No. 62/293,982, filed on Feb. 11, 2016.

(51) Int. Cl.
*C12Q 1/68* (2018.01)
*C12Q 1/6874* (2018.01)
*C12Q 1/6869* (2018.01)

(52) U.S. Cl.
CPC ......... *C12Q 1/6874* (2013.01); *C12Q 1/6869* (2013.01)

(58) Field of Classification Search
CPC ................ C12Q 1/6869; C12Q 1/6874; C12Q 2535/113; C12Q 2563/107
See application file for complete search history.

(56) References Cited

U.S. PATENT DOCUMENTS

| | | | |
|---|---|---|---|
| 6,664,079 B2 | 12/2003 | Ju et al. | 435/91.1 |
| 9,145,589 B2 | 9/2015 | Gordon et al. | 435/6.1 |
| 2011/0046091 A1* | 2/2011 | Cau | A61K 31/22 514/108 |
| 2014/0163368 A1* | 6/2014 | Rousso | A61B 6/037 600/436 |

OTHER PUBLICATIONS

Chyan, Y.-J. et al. (1999) "Potent Neuroprotective Properties against the Alzheimer β-Amyloid by an Endogenous Melatonin-related Indole Structure, Indole-3-propionic Acid," *Journal of Biological Chemistry* 274(31), 21937-21942.

Martin, J. P. et al. (1987) "The role of oxygen radicals in dye-mediated photodynamic effects in *Escherichia coli* B," *Journal of Biological Chemistry* 262(15), 7213-7219.

* cited by examiner

*Primary Examiner* — David C Thomas
(74) *Attorney, Agent, or Firm* — Medlen and Carrol, LLP

(57) ABSTRACT

The invention relates to methods, compositions, devices, systems and kits are described including, without limitation, reagents and mixtures, for determining the identity of nucleic acids in nucleotide sequences using, for example, data obtained from sequencing by synthesis methods.

9 Claims, 12 Drawing Sheets

(1 of 12 Drawing Sheet(s) Filed in Color)

| Station | Step | Volume [µl] | Pump Speed [µl/s] | Pump Time [s] | Dwell Time [s] | Total Time Per Station [s] |
|---|---|---|---|---|---|---|
| 1 | Cleave | 100 | 67 | 1.5 | 120 | 121 |
| 2 | Dwell | 0 | 0 | 0.0 | 120 | 120 |
| 2 | Wash11 | 990 | 27 | 36.7 | 0 | 37 |
| 3 | ExtA | 100 | 67 | 1.5 | 120 | 121 |
| 4 | ExtB | 100 | 67 | 1.5 | 150 | 151 |
| 5 | Wash | 330 | 27 | 12.2 | 0 | 12 |
| 5 | ImgAB* (100 each) | 200 | 27 | 7.4 | 0 | 7 |
| 11 | Imaging** | 0 | 0 | 0.0 | 560 | 560 |
| 20 | Wash | 330 | 27 | 12.2 | 0 | 12 |

ADDITIVES TO IMPROVE SEQUENCING BY SYNTHESIS PERFORMANCE

FIELD OF THE INVENTION

The invention relates to methods, compositions, devices, systems and kits are described including, without limitation, reagents and mixtures, for determining the identity of nucleic acids in nucleotide sequences using, for example, data obtained from sequencing by synthesis methods.

BACKGROUND OF THE INVENTION

Over the past 25 years, the amount of DNA sequence information that has been generated and deposited into Genbank has grown exponentially. Traditional sequencing methods (e.g., for example Sanger sequencing) are being replaced by next-generation sequencing technologies that use a form of sequencing by synthesis (SBS), wherein specially designed nucleotides and DNA polymerases are used to read the sequence of chip-bound, single-stranded DNA templates in a controlled manner. To attain high throughput, many millions of such template spots are arrayed across a sequencing chip and their sequence is independently read out and recorded.

Systems for using arrays for DNA sequencing are known (e.g., Ju et al., U.S. Pat. No. 6,664,079, hereby incorporated by reference). However, there is a continued need for methods and compositions for increasing the accuracy and/or efficiency of sequencing.

SUMMARY OF THE INVENTION

The invention relates to methods, compositions, devices, systems and kits as described herein including, without limitation, reagents, and mixtures, for reducing lead during nucleic acid sequencing. While not intended to be limited to any particular mechanism, it is believed that sequencing is improved and error rates are reduce by the use of a nucleotide binding site competitor, i.e. a compound that competes with nucleotides for binding sites.

In one embodiment, the invention contemplates a method of incorporating nucleotides, comprising: a) providing i) a plurality of nucleic acid primers and template molecules, ii) an extend reagent comprising polymerase and a plurality of nucleotide analogues, and iii) a wash reagent comprising methylenediphosphonic acid; b) hybridizing at least a portion of said primers to at least a portion of said template molecules so as to create hybridized primers; c) exposing said hybridized primers to said extend reagent under conditions such that a first nucleotide analogue is incorporated into at least a portion of said hybridized primers so as to create extended primers comprising an incorporated nucleotide analogue; d) washing said extended primers with said wash reagent. In one embodiment, said incorporated nucleotide analogue comprises a label attached through a cleavable disulfide linker to the base. In one embodiment, said label is fluorescent. In one embodiment, said extend reagent further comprises cystamine. In one embodiment, said method further comprises: e) detecting said label of a first labeled nucleotide analogue. In one embodiment, said detecting of step e) is performed in the presence of methylenediphosphonic acid. In one embodiment, the concentration of said methylenediphosphonic acid is between 0.1 mM and 4 mM. In one embodiment, the concentration of said methylenediphosphonic acid is between 0.25 mM and 1 mM. In one embodiment, the concentration of said methylenediphosphonic acid is between 0.35 mM and 0.65 mM (e.g. 0.5 mM).

In one embodiment, the invention contemplates a wash reagent comprising a nucleotide binding site competitor such as methylenediphosphonic acid in a buffer. In one embodiment, said buffer is a Tris buffer. In one embodiment, the present invention contemplates a kit with this wash reagent as one of the components.

In one embodiment, the invention contemplates a system comprising primers hybridized to template in solution, said solution comprising a nucleotide binding site competitor such as methylenediphosphonic acid. In one embodiment, said hybridized primers and template are immobilized. In one embodiment, said hybridized primers and template are in a flow cell.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "plurality" means two or more.

The term "nucleotide sequence" refers to a polymer comprising deoxyribonucleotides (in DNA) or ribonucleotides (in RNA).

The term "interrogation position" when made in reference to a nucleotide sequence refers to a location of interest in the sequence, such as the location at which the identity of a nucleic acid is sought to be determined.

The terms "probe" and "label" are interchangeably used to describe a chemical moiety that, when attached to a composition of interest, acts as a marker for the presence of the composition of interest. Probes are exemplified by fluorescent moieties such as 5-carboxyfluorescein, 6-carboxyrhodamine-6G, N,N,N',N'-tetramethyl-6-carboxyrhodamine, and 6-carboxy-X-rhodamine. Probes also include a fluorescence energy transfer tag that comprises an energy transfer donor and an energy transfer acceptor. The energy transfer donor is exemplified by 5-carboxyfluorescein and cyanine (3 or 3.5), and the energy transfer acceptor is exemplified by dichlorocarboxyfluorescein, dichloro-6-carboxyrhodamine-6G, dichloro-N,N,N',N'-tetramethyl-6-carboxyrhodamine, and dichloro-6-carboxy-X-rhodamine. The mass tag is exemplified by a 2-nitro-a-methyl-benzyl group, 2-nitro-a-methyl-3-fluorobenzyl group, 2-nitro-a-methyl-3,4-difluorobenzyl group, and 2-nitro-a-methyl-3,4-dimethoxybenzyl group. Cyanine 5 and 5.5 are acceptors.

The term "probe corresponds to a nucleotide" means that the probe serves as a marker for the presence of the nucleotide. Thus, detecting the presence of the probe also detects the presence of the nucleotide.

The term "field flattening" when in reference to pixel intensity of an image refers to reducing differences in pixel intensity between two or more pixels at different spatial locations on the image of a uniformly radiating surface.

The terms "reducing," "decreasing" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is lower than in the second sample by any amount that is statistically significant using any art-accepted statistical method of analysis. In some embodiments, the quantity of molecule and/or phenomenon in the first sample is at least 10% lower than, at least 25% lower than, at least 50% lower than, at least 75% lower than, and/or at least 90% lower than the quantity of the same molecule and/or phenomenon in a second sample. The term "reducing" includes, but does not require, a 100% lowering in the quantity of the molecule and/or phenomenon in the first sample compared to the second sample.

The terms "increasing," "elevating" and grammatical equivalents when in reference to the level of a molecule and/or phenomenon (e.g., light intensity, chemical concentration, correlation between two event, etc.) in a first sample relative to a second sample, mean that the quantity of molecule and/or phenomenon in the first sample is higher than in the second sample by any amount that is statistically significant using any art-accepted statistical method of analysis. In some embodiments, the quantity of the molecule and/or phenomenon in the first sample is at least 10% greater than, at least 25% greater than, at least 50% greater than, at least 75% greater than, and/or at least 90% greater than the quantity of the same molecule and/or phenomenon in a second sample.

"Spectral" is a term that refers to electromagnetic radiation. In one embodiment, the electromagnetic radiation is in the visible light region (wavelength of approximately 400-700 nanometers), such as that emitted by fluorescent moieties.

The terms "spectral filter" and "color filter" are interchangeably used to refer to a filter for detection of a particular range of electromagnetic wavelengths, such as in the visible region, thereby. The terms "spectral crosstalk" and "color crosstalk" refer to any phenomenon by which a spectral signal, or a digital signal that corresponds to a spectral signal, that is transmitted and measured in one channel of transmission creates an undesired effect in another channel. For example, spectral crosstalk may occur when exciting only a green dye, resulting in a signal that is visible in the yellow channel as well as in the green channel. Using methods disclosed herein, if this spectral crosstalk is calibrated, it may be removed from subsequent measurements even if the dyes are mixed in unknown quantities.

The term "low pass filter" refers to a filter that passes signals but reduces signals with higher spatial variation than a desired cutoff value. A low pass filter passes wavelengths below a certain cutoff and absorbs wavelength above the cutoff.

One element is in "fluid communication" or "fluidic communication" with another element when it is attached through a channel, tube or other conduit that permits the passage of liquid, gas, vapor and the like. "Tubing" can be made of a variety of materials, including put not limited to various plastics, metals and composites. Tubing can be rigid or flexible. Tubing can be "attached" in a detachable mode or a fixed mode. Tubing is typically attached by sliding into or over (both of which are examples of "slidably engaging") other tubing or connectors.

The term "methylenediphosphonic acid" or "medronic acid" or "PcPi" refers to a compound with the linear formula $CH_2[P(O)(OH)_2]_2$ with the structure:

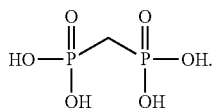

DESCRIPTION OF THE FIGURES

The patent or application file contains at least one drawing executed in color. Copies of this patent or patent application publication with color drawing(s) will be provided by the Office upon request and payment of the necessary fee.

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 12 shows potential steps of a sequence-by-synthesis (SBS) method.

DETAILED DESCRIPTON OF THE INVENTION

Figure 1:
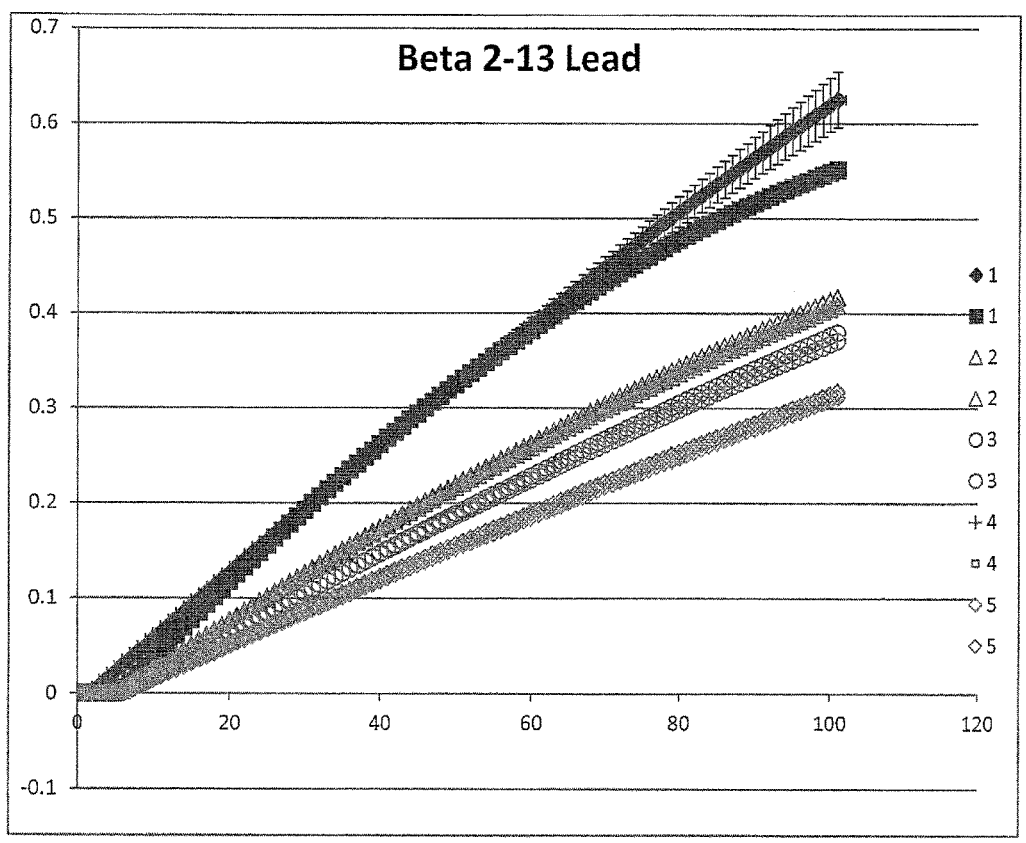
FIG. 1 is a graph showing sequencing results under various conditions. Each condition had two flow cells, so each condition is depicted on the graph. Condition 1 was wherein the delivery is 100 μl and there is 1 mM iodoacetamide, 10 mM cystamine, and 1×SSC. Condition 2 was wherein the delivery is 200 μl and chem 4 conditions. Chem 4 refers to the baseline chemistry at the time, to which we were trying to make improvements. Chem 4 has 200 μl reagent volume delivery, reagents described in Sequencing by synthesis (see Table 1), except there was no PcPi in the wash buffers. Condition 3 was wherein the delivery is 100 μl and there is 1 mM PcPi in wash 1 and 2. Condition 4 was wherein the delivery is 100 μl and there is 1 mM PcPi in wash 1 and 2. Condition 5 was wherein the delivery is 200 μl and there is 1 mM PcPi in wash 1 and 2. The results indicate 1) Iodoacetamide in Wash 11 did not reduce the lead, conditions: 1 mM iodoacetamide, 10 mM cystamine, 1×SSC. 2) Chem 4 baseline has lead on 0.4 at 100 cycles; 3) Addition of 1 mM PcPi in washes 1 and 2 reduces lead to baseline levels. 4) Repeat addition of 1 mM PcPi with same result. Addition of 1 mM PcPi and 200 μl delivery reduces lead even more.
Figure 2:
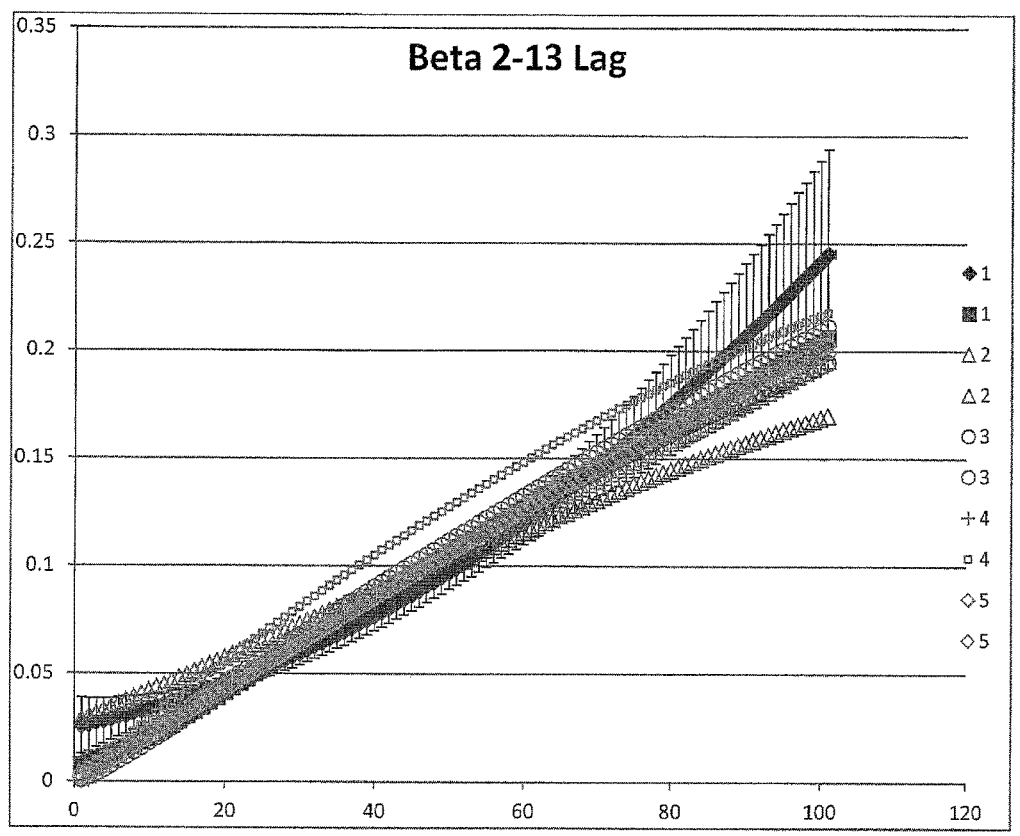
FIG. 2 shows Run Results Chem 4, Beta 2-13 Lag. Each condition had two flow cells, so each condition is depicted on the graph. Condition 1 was wherein the delivery is 100 μl and there is 1 mM iodoacetamide, 10 mM cystamine, and 1×SSC. Condition 2 was wherein the delivery is 200 μl and chem 4 conditions. Condition 3 was wherein the delivery is 100 μl and there is 1 mM PcPi in wash 1 and 2. Condition 4 was wherein the delivery is 100 μl and there is 1 mM PcPi in wash 1 and 2. Condition 5 was wherein the delivery is 200 μl and there is 1 mM PcPi in wash 1 and 2. All conditions have little or no effect on Lag.
Figure 3:
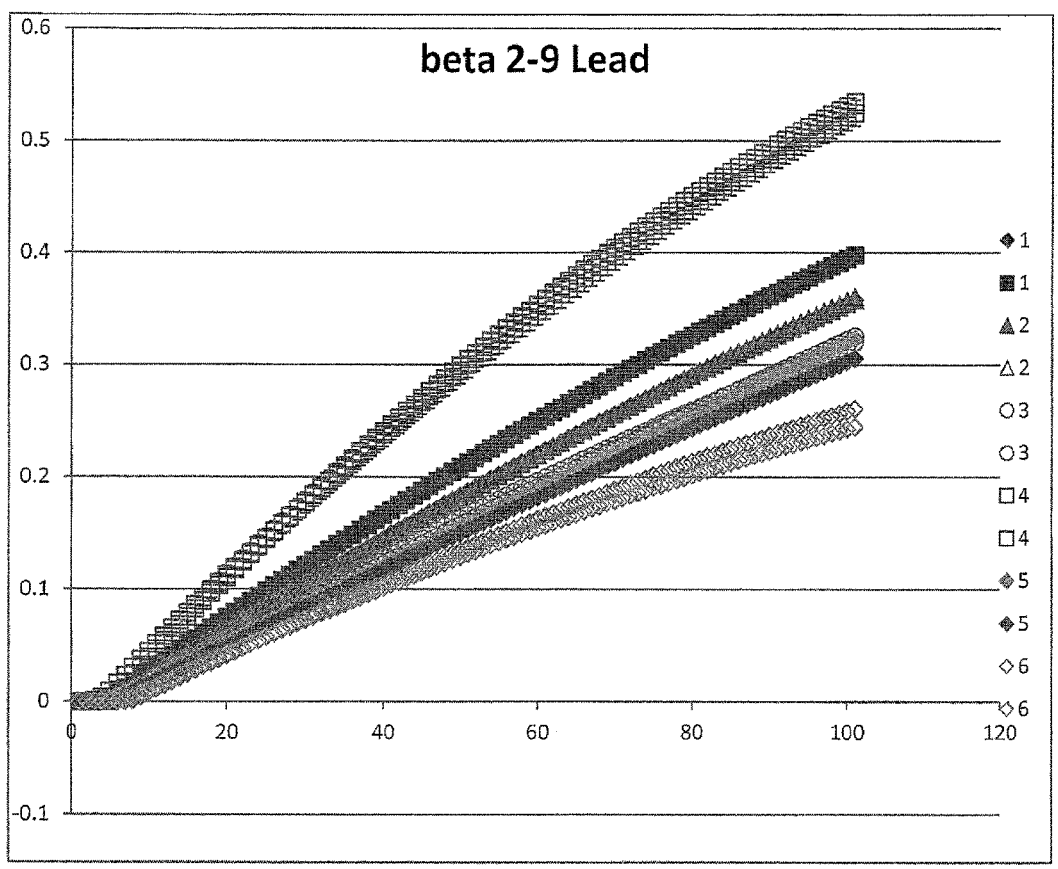
FIG. 3 shows Run Results Chem 4, Beta 2-9 Lead. Each condition had two flow cells, so each condition is depicted on the graph. Condition 1 was wherein the delivery is 100 μl and there is 1 mM PcPi in wash 1 and 2. Condition 2 was wherein the delivery is 200 μl and chem 4 conditions. Condition 3 was wherein the delivery is 100 μl and there is 1 mM PcPi in wash 1 and 2. Condition 4 was wherein the delivery is 100 μl and there is 10 mM cystamine in Exted A. Condition 5 was wherein the delivery is 100 μl and there is 1 mM PcPi in wash 1 and 2. Condition 3 was wherein the delivery is 100 μl and there is 2×Nucs ExtA, 1 mM PcPi in wash 1 and 2. It is believed that in condition 1 the addition of 1 mM PcPi in washes 1 and 2 reduces lead to baseline levels. It is believed that in condition 2 the Chem 4 baseline has lead of 0.4 at 100 cycles. It is believed that in condition 3 and 4 the 1 mM PcPi in wash 1 and 2, Addition of 10 mM Cystamine in Extend A did not reduce lead. It is believed that in condition 5 repeat addition of 1 mM PcPi gave the same result. It is believed that in condition 6 wash 1 and 2, the addition of 1 mM PcPi and 2× Nuc in ExtA reduces lead even more wash 1 and 2. It is believed that there is no observed impact on lag for any condition tested.
Figure 4:
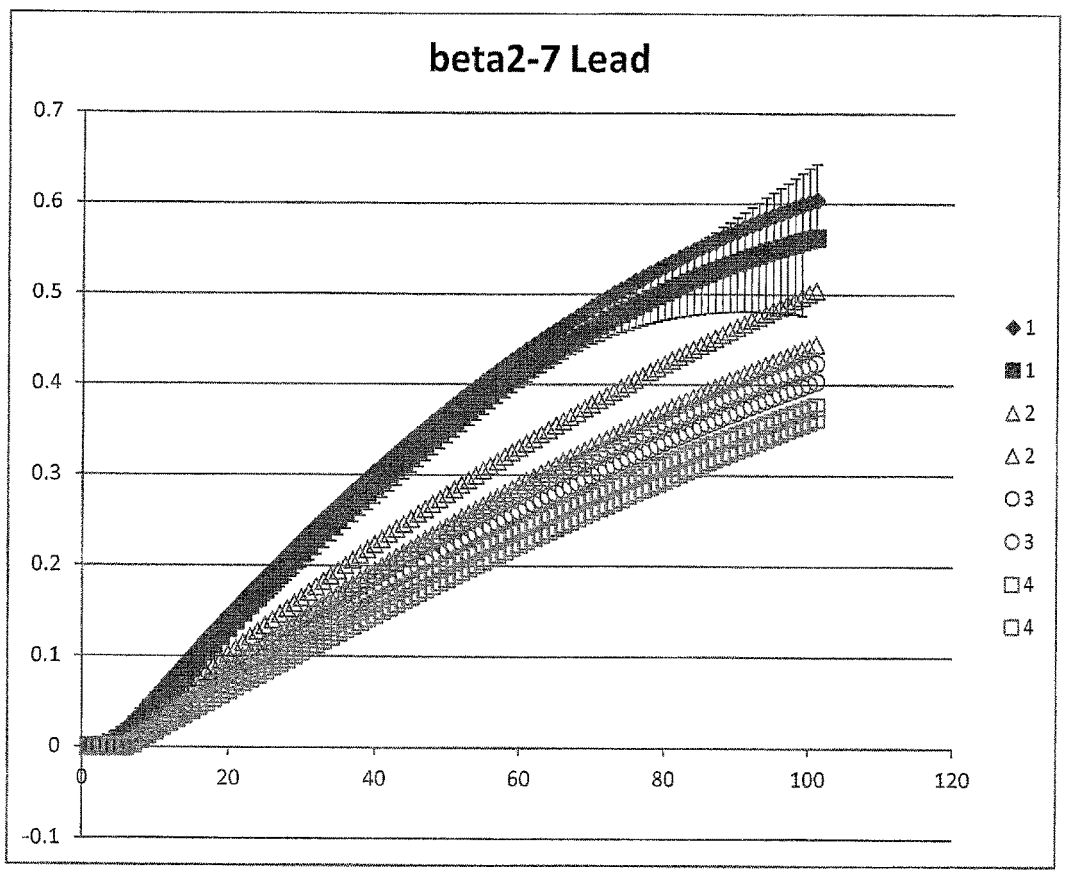
FIG. 4 shows Run Results Chem 4, Beta 2-7 Lead. Each condition had two flow cells, so each condition is depicted on the graph. Condition 1 was wherein the delivery is 100 µl and there is 10 mM azido acetate in Extend A. Condition 2 was wherein the delivery is 200 µl and and chem 4 conditions. Condition 3 was wherein the delivery is 100 µl and there is 1 mM PcPi in wash 1 and 2. Condition 4 was wherein the delivery is 100 µl and there is 4 mM PcPi in wash 1 and 2. It is believed that in condition 1 the addition of 10 mM Azido acetate in Extend A did not reduce lead to baseline levels. It is believed that in condition 2 the Chem 4 baseline has lead on 0.4 at 100 cycles. It is believed that in condition 3 the wash 1 and 2 addition of 1 mM PcPi in washes 1 and 2 reduces lead to baseline levels. It is believed that in condition 4, wash 1 and 2, the addition of 4 mM PcPi in washes 1 and 2 reduces lead even more. There is no observed impact on lag for any condition tested.

Next generation sequencing results are impacted by sequence phasing. Phasing has two components Lead and Lag, and both components have a negative impact on sequencing results. Current wash solutions do not contain any component capable of reducing undesired nucleotide binding, by competeing for nucleotide binding sites. Therefore, there is a continued need for a wash solution that is capable of reducing undesired binding of nucleotides.

Including methylenediphosphonic acid (PcPi) in one or more of the wash buffers reduces lead. While not limited to any particular mechanism, it is believed that methylenediphosphonic acid competes with nucleotides for the binding sites on the sequencing support matrix and any remaining DNA polymerase that did not wash away.

DNA sequence is determined by a method of sequencing by synthesis. The DNA sequence is determined by multiple cycles of chemistry on the instrument. While a variety of sequencing instruments can be used (Applied Biosystems SOLiD System, Illumina Next-Generation Sequencing Platforms, OLiD/Ion Torrent PGM from Life Sciences, Genome Analyzer/HiSeq 2000/MiSeq from Illumina, and GS FLX Titanium/GS Junior from Roche, Ion Proton™ System from ThermoFisher Scientific, QIAGEN's GeneReader DNA sequencing system, and other next generation sequencers), a preferred instrument is QIAGEN's GeneReader DNA sequencing system. Each cycle of sequencing consists of eight steps: extension 1, extension 2, wash 1, addition imaging solution, imaging, wash 2, cleave, and wash 3. Data collected during imaging cycles is processed by analysis software yielding error rates, throughput values, and applied phasing correction values.

The volume of reagent used in the extension steps was found to have an impact on sequencing results. When the volume was halved, the lead component of phasing increased. When the volume was halved and 1 mM methylenediphosphonic acid was added to washes 1 and 2, the lead component of phasing was reduced to the level found with the full volume addition.

Although it is not necessary to understand the mechanism of an invention, it is believed that using methylenediphosphonic acid in Wash B allows delivery volume to be reduced to 100 µl. In one embodiment, this will allow four flow cell runs. Addition of reagents to remove TCEP, did not improve high lead (see FIG. 1, FIG. 2, FIG. 3, and FIG. 4).

Figure 5:
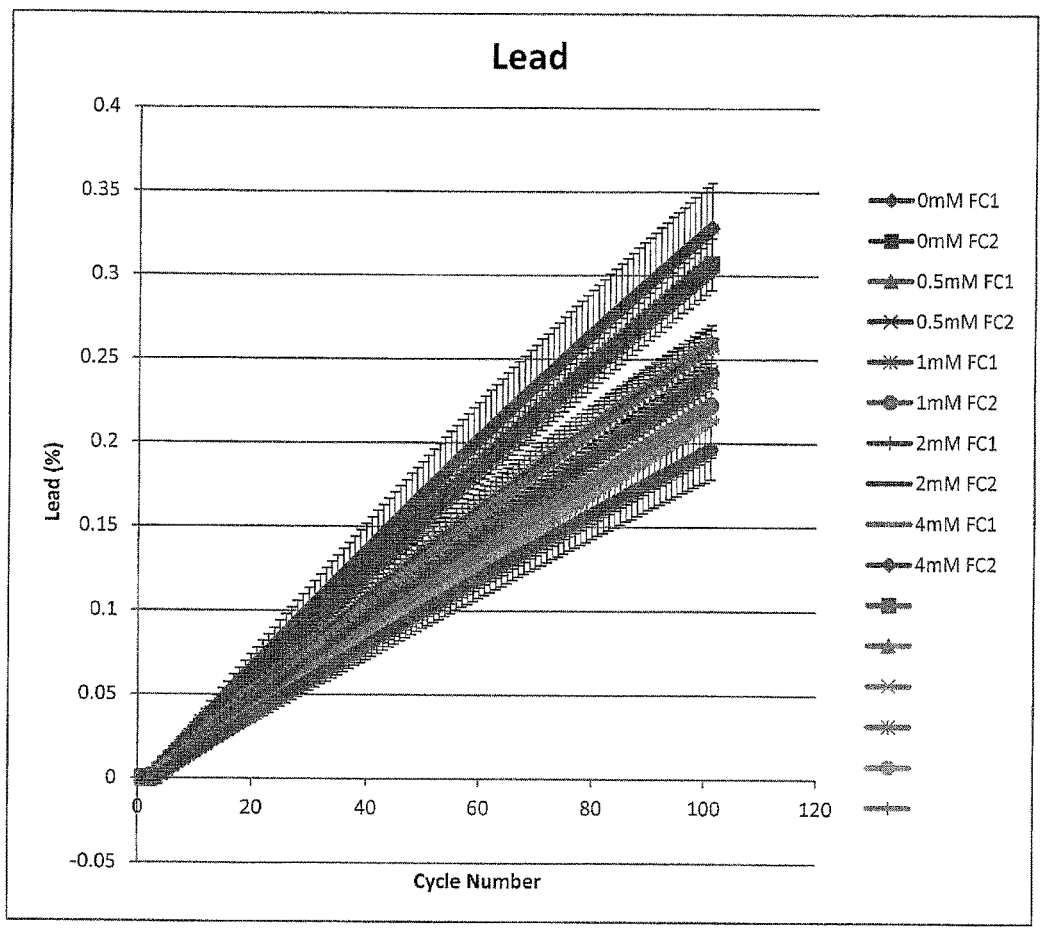
FIG. 5 shows 100 cycle clone Runs on beta6.4, with 10 variable concentrations of PcPi in Washes 1 and 2, including 0 mM, 0.5 mM, 1 mM, 2 mM, and 4 mM PcPi. GRA analysis with results compiled with DIT max ver 25. It is believed that there is a correlation between PcPi concentration and Lead.
Figure 6:
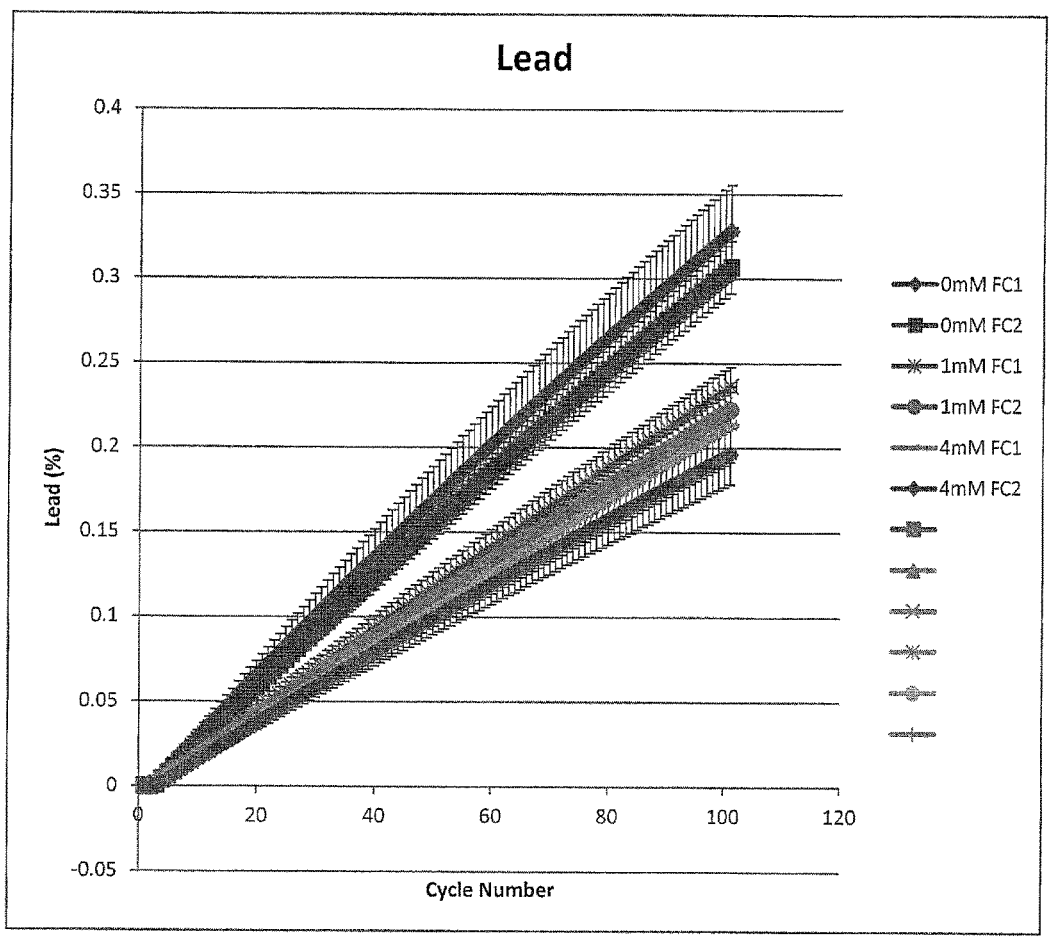
FIG. 6 shows 100 cycle clone Runs on beta6.4, with 6 variable concentrations of PcPi in Washes 1 and 2, including 0 mM, 1 mM, and 4 mM PcPi. GRA analysis with results compiled with DIT max ver 25. It is believed that there is an improvement from 1 mM to 4 mM, is incremental.

Experiments were undertaken to determine the impact of varying concentrations of methylenediphosonic acid on lead. The concentration of methylenediphosphonic acid was 0 mM, 0.5 mM, 1 mM, 2 mM and 4 mM in washes 1 and 2 (bottles 9 and 10) (see FIG. 5). Runs of 100 cycles were performed and analyzed. The results showed that increasing the concentration of methylenediphosphonic acid in Washes 1 and 2, reduces lead. The largest impact (e.g. change) was found when increasing from 0 mM to 0.5 mM. Incremental improvements were observed with greater concentrations up to 4 mM (see FIG. 4, FIG. 5, and FIG. 6). A concentration of 1 mM was chosen to maximize the reduction of lead and because there was no observable impact on the other key performance indicators when concentrations were increased from 1 mM to 4 mM.

Figure 7:
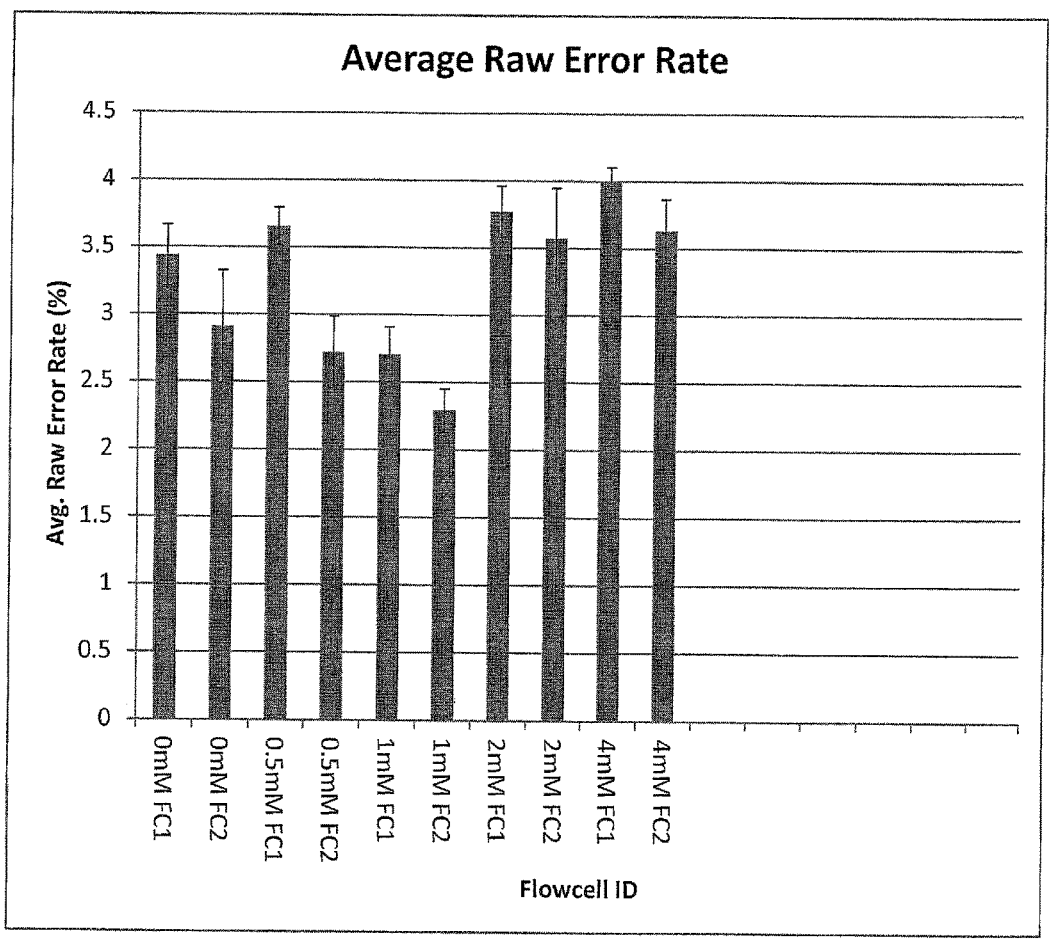
FIG. 7 shows the Average Raw Error Rate for 100 cycle clone Runs on beta6.4, with variable concentrations of PcPi in Washes 1 and 2. GRA analysis with results compiled with DIT max ver 25, There is no Correlation between PcPi concentration and raw error rate.
Figure 8:
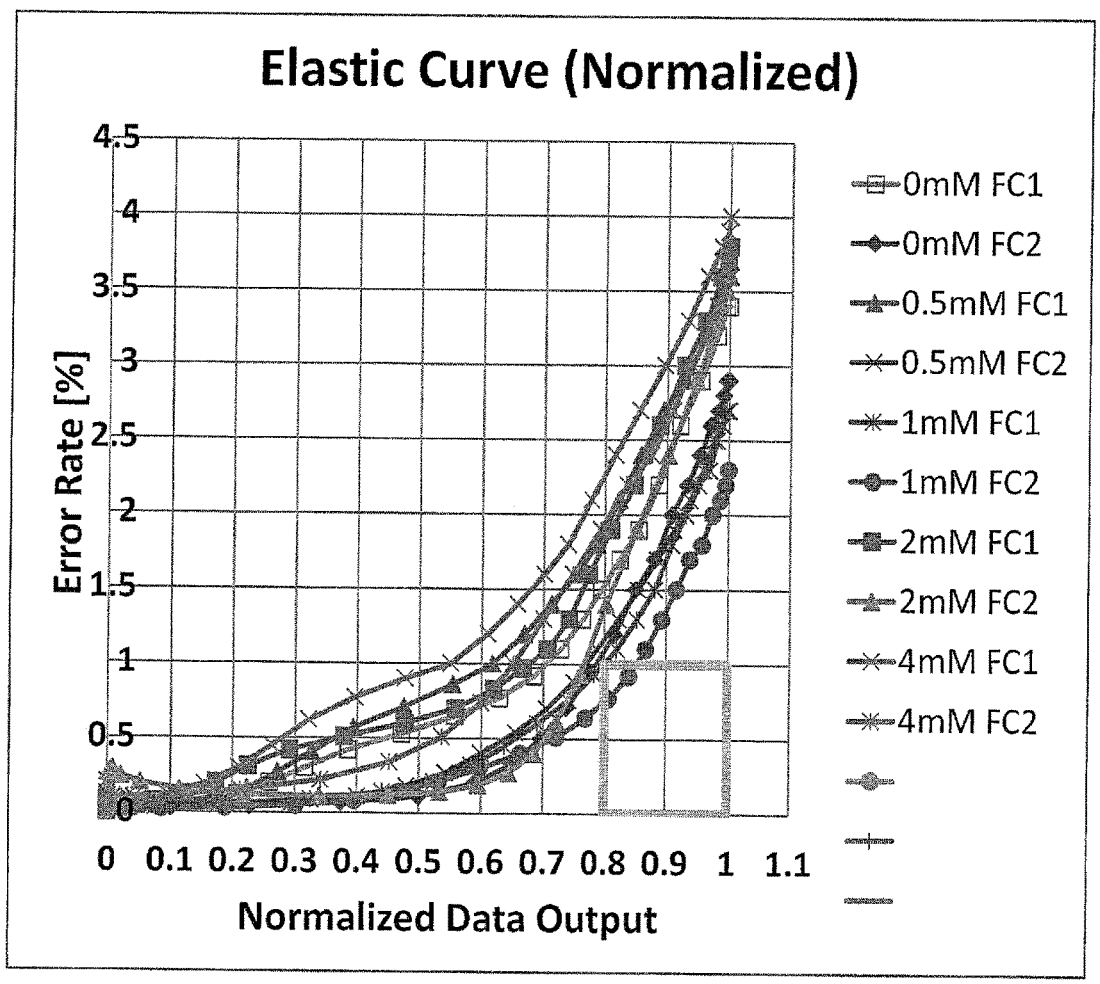
FIG. 8 shows the Elastic Curve (Normalized) for 100 cycle clone Runs on beta6.4, with variable concentrations of PcPi in Washes 1 and 2. GRA analysis with results compiled with DIT max ver 25. No Correlation between PcPi concentration and Elastic Curve results.
Figure 9:
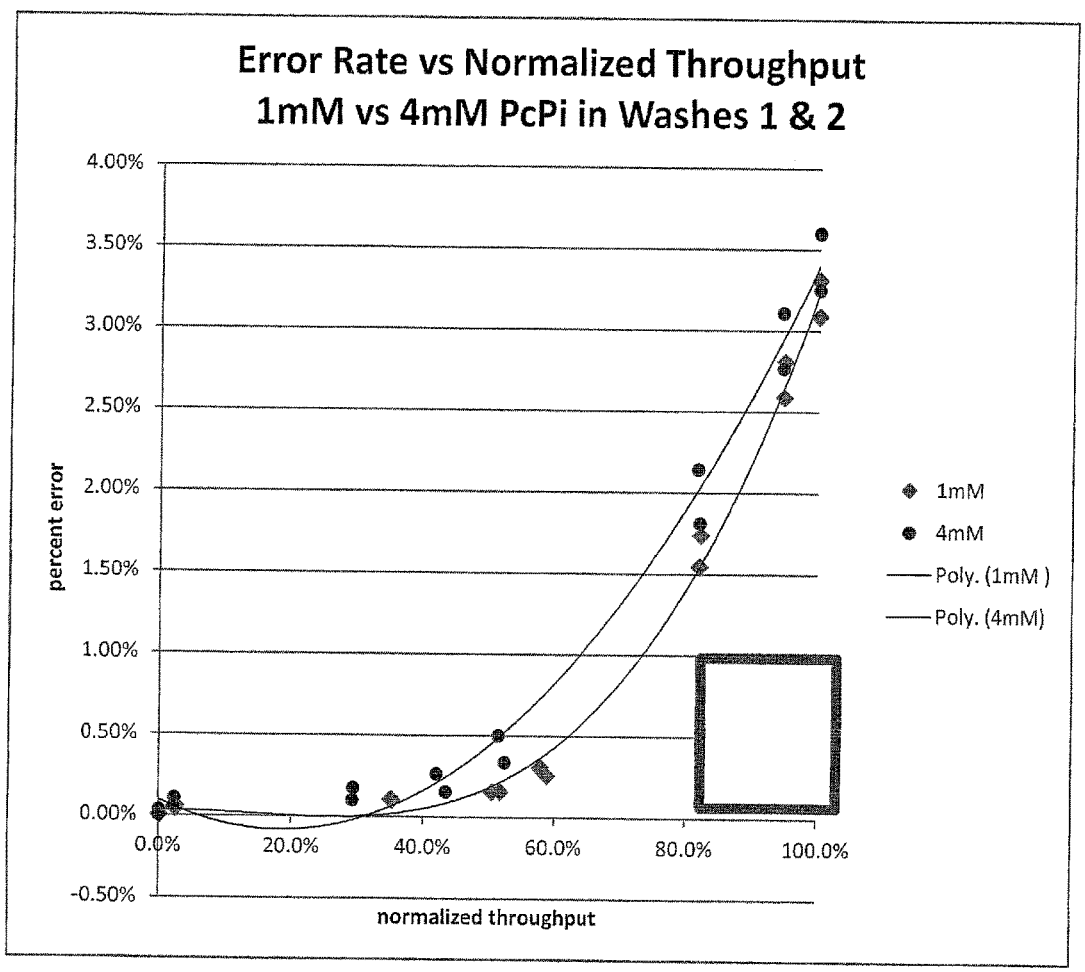
FIG. 9 shows the Error Rate vs Normalized Throughput 1 mM vs 4 mM PcPi in Washes 1 and 2. 100 cycle clone Runs on beta6.4, with variable concentrations of PcPi in Washes 1 and 2. GRA analysis with Mapchecker 7.44 elastic curve. There is no difference detected in mapchecker elatic curves.
Figure 10:
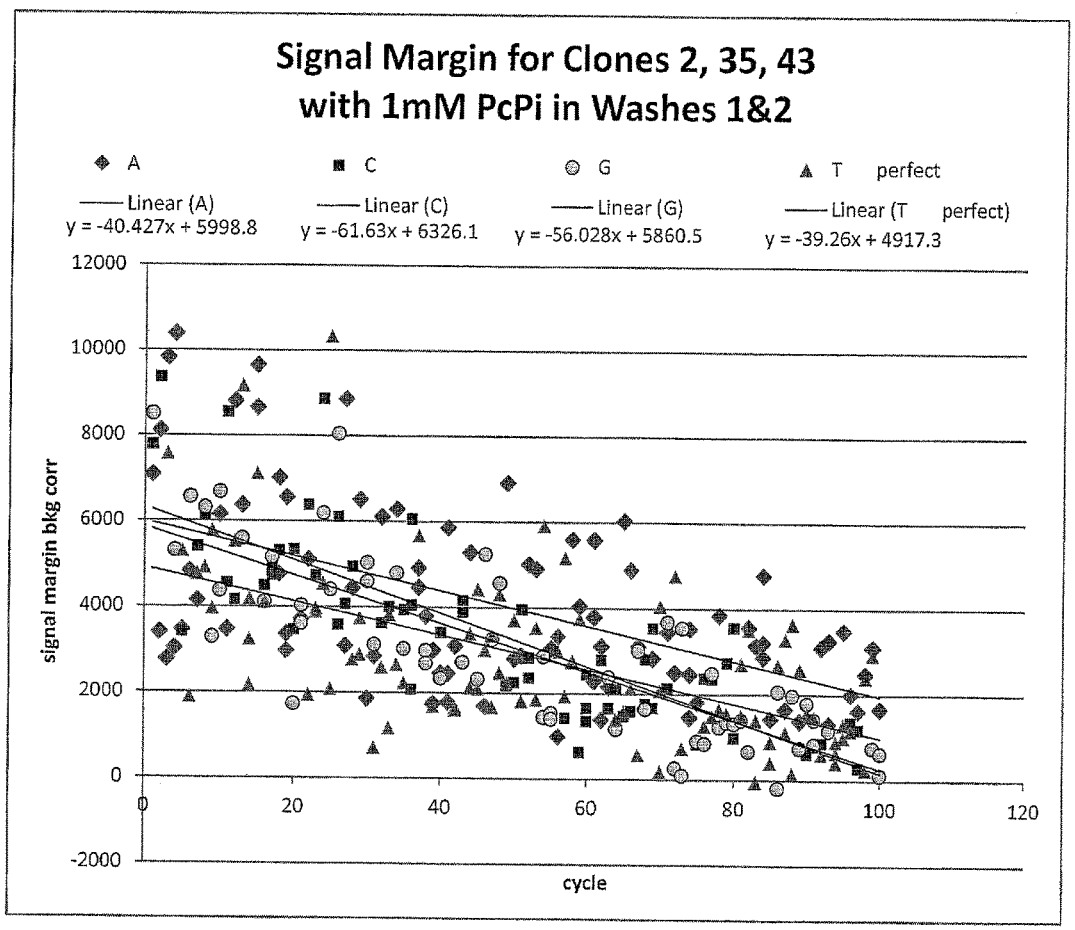
FIG. 10 shows the Signal Margin for Clones 2, 35, 43 with 1 mM PcPi in Washes 1 and 2. 100 cycle clone Runs on beta6.4, with variable concentrations of PcPi in Washes 1 and 2. Access CollectSignalInt V1.0, Signal Margin bkg con; Clones 2, 35, 43. Tiles 0, 10, 20, 30. Standard 1 mM PcPi has a few calls with negative signal margins between cycle 80 and 100. Signal Margin decreases with cycle number.
Figure 11:
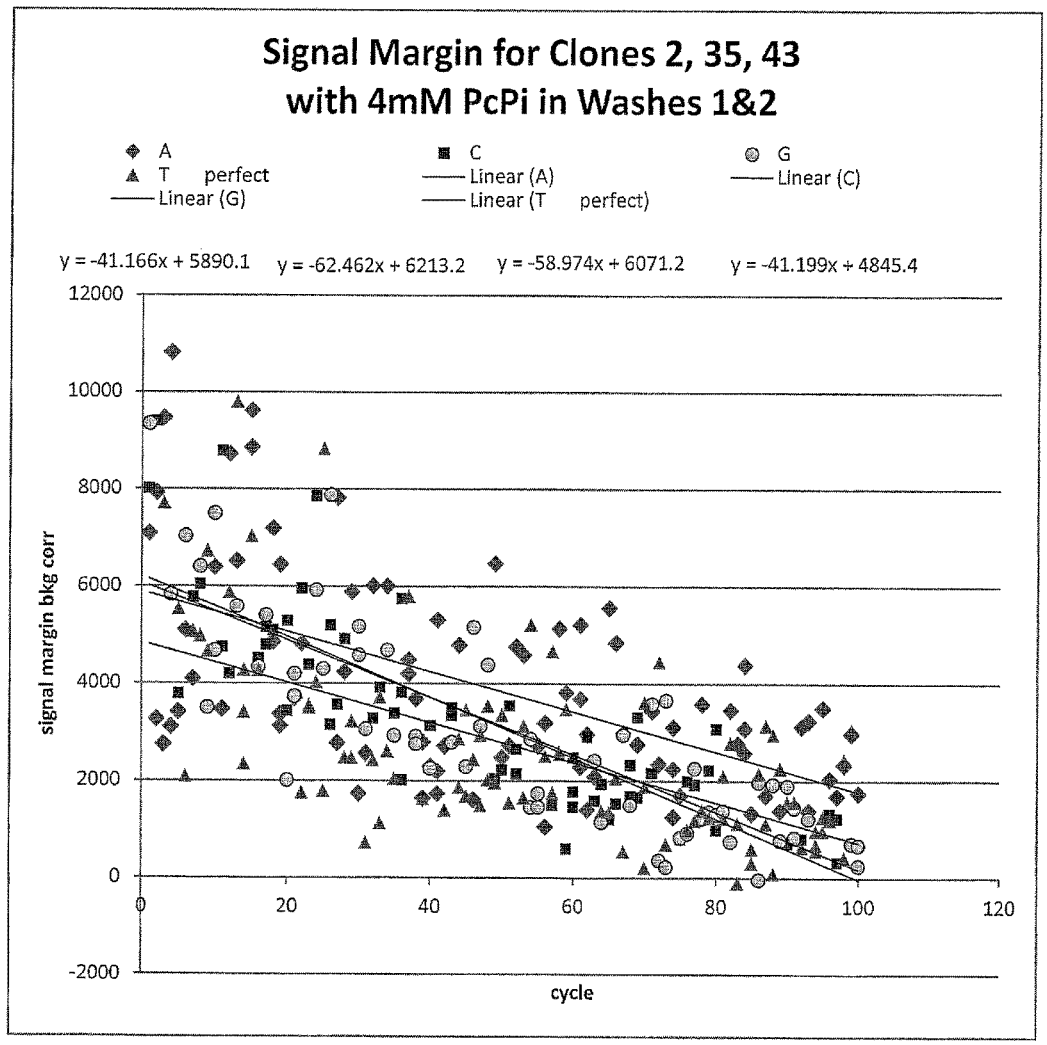
FIG. 11 shows the Signal Margin for Clones 2, 35, 43 with 4 mM PcPi in Washes 1 and 2. 100 cycle clone Runs on beta6.4, with variable concentrations of PePi in Washes 1 and 2. Access CollectSignalInt V1.0; Signal Margin bkg con; Clones 2, 35, 43. Tiles 0, 10, 20, 30. 4 mM PcPi also has a few calls with negative signal margins between cycle 80 and 100. Signal Margin decreases with cycle number. Increased PcPi has no impact.

In one embodiment, the present invention contemplates a method comprising methylenediphosphonic acid, a potent competitor with nucleotides for the binding sites on the sequencing support matrix and any remaining DNA polymerase, as an additive to wash buffers to reduce lead in sequencing by synthesis (SBS). Although it is not necessary to understand the mechanism of an invention, it is believed that the presently disclosed method provides a source of competition (by the addition of methylenediphosphonic acid to the wash buffer) thereby reducing lead in sequencing by synthesis (SBS). It is not intended that the present invention be limited to use of methylenediphosphonic acid to only the wash reagents. In one embodiment, the present invention contemplates the use of this compound in other sequencing steps, including but not limited the steps of imaging and base calling, will result in reduced error rates (see FIG. 7, FIG. 8, and FIG. 9).

I. Sequencing-By Synthesis (SBS)

It is not intended that the present invention be limited to any particular series of steps or protocols for sequencing. In one embodiment, the present invention contemplates a SBS method comprising the steps shown in Table 1.

TABLE 1

One SBS Embodiment

| | | Fluid Movements | | | | |
|---|---|---|---|---|---|---|
| Step | Reagent | Volume mL | Speed mL/s | Station Number | Temp ° C. | Time [s] |
| 1. Dispense Reagent | Reagent 1 | 100 | 67 | 3 | 65 | 7 |
| 2. Incubate Reagent | Reagent 1 | n/a | n/a | 3 | 65 | 210 |
| 3. Dispense Reagent | Reagent 2 | 100 | 67 | 4 | 65 | 7 |
| 4. Incubate Reagent | Reagent 2 | n/a | n/a | 4 | 65 | 210 |
| 5. Dispense Reagent | Reagent 3 | 330 | 27 | 5 | Ambient | 12 |
| 6. Dispense Reagent | Reagent 4 + 5 | 200 | 27 | 5 | Ambient | 15 |
| 7. Image | n/a | n/a | n/a | 11 | Ambient | 210 |
| 8. Dispense Reagent | Reagent 3 | 330 | 27 | 20 | 65 | 12 |
| 9. Dispense Reagent | Reagent 6 | 100 | 67 | 1 | 65 | 7 |
| 10. Incubate Reagent | Reagent 6 | n/a | n/a | 1 | 65 | 210 |
| 11. Incubate Reagent | Reagent 6 | n/a | n/a | 2 | 65 | 210 |
| 12. Dispense Reagent | Reagent 7 | 990 | 27 | 2 | 65 | 37 |
| 13. Go to Step 1 | | | | | | |

Reagent 1 = Extend A;
Reagent 2 = Extend B;
Reagent 3 = Wash;
Reagent 4 = Image A;
Reagent 5 = Image B;
Reagent 6 = Cleave; and
Reagent 7 = Wash 11

It is not intended that the present invention be limited to any particular wash reagent. A variety of wash reagents are contemplated. In one embodiment, washing solution compositions may include, but are not limited to:

| | Component | Conc |
|---|---|---|
| Wash (1, 2) | Tween | 0.05% |
| | TrisHCl (pH 8.8) (mM) | 50 |
| | NaCl (mM) | 50 |
| | EDTA (mM) | 1 |
| | Methylenediphosphonic acid (PcPi) (mM) | 1 |
| Wash (11) | Tween | 0.05% |
| | TrisHCl (pH 8.8) (mM) | 50 |
| | NaCl (mM) | 50 |
| | EDTA (mM) | 1 |
| | Cystamine (mM) | 10 |

The present invention contemplates that the steps of the method can be associated with stations in an automated sequencing machine. See U.S. Pat. No. 9,145,589, hereby incorporated by reference. In one embodiment, the SBS method comprises a cycle including, but not limited to, the steps of:

A. Extension Step

In one embodiment, the present invention contemplates a series of method steps, which an instrument for automated sequencing by synthesis may carry out. In one embodiment, the process is comprised of the following reagent reservoirs (see, Table 1):

1) Extend A comprising reversibly terminated labeled nucleotides and polymerase.

The composition of Extend A is as follows:

| Component | Conc |
|---|---|
| PNSE (% wt/vol) | 0.005% |
| Tris x HCl (pH 8.8), mM | 50 |
| NaCl (mM) | 50 |

-continued

| Component | Conc |
|---|---|
| EDTA (mM) | 1 |
| MgSO4 (mM) | 10 |
| Cystamine (mM) | 1 |
| Glycerol (% wt/vol) | 0.01% |
| Therminator IX (U/ml) | 10* |
| N3-dCTP (μM) | 3.83 |
| N3-dTTP (μM) | 3.61 |
| N3-dATP (μM) | 4.03 |
| N3-dGTP (μM) | 0.4 |
| Alexa488-dCTP (nM) | 550 |
| R6G-dUTP (nM) | 35 |
| ROX-dATP (nM) | 221 |
| Cy5-dGTP (nM) | 66 |

*With alkylated free Cys - see SOP

2) Extend B comprising reversibly terminated unlabeled nucleotides and polymerase, but lacking labeled nucleotide analogues. The composition of Extend B is as follows:

| Component | Conc |
|---|---|
| PNSE (% wt/vol) | 0.005% |
| Tris x HCl (pH 8.8), mM | 50 |
| NaCl (mM) | 50 |
| EDTA (mM) | 1 |
| MgSO4 (mM) | 10 |
| Glycerol (% wt/vol) | 0.01% |
| Therminator IX (U/ml) | 10* |
| N3-dCTP (µM) | 21 |
| N3-dTTP (µM) | 17 |
| N3-dATP (µM) | 21 |
| N3-dGTP (µM) | 2 |

*With alkylated free Cys - see SOP

3) Wash solution 1 (e.g. in one embodiment comprising a detergent, such as polysorbate 20, in a citrate solution, such as saline sodium citrate);
4) Cleave solution. A cleaving solution composition is as follows:

| | Component | Conc |
|---|---|---|
| Cleave | NaOH (mM) | 237.5 |
| | TrisHCl (pH 8.0) (mM) | 237.5 |
| | TCEP (mM) | 50 |

5) Wash solution 2 (e.g. in one embodiment, comprising a detergent, such as polysorbate 20 in a buffer comprising tris(hydroxymethyl)aminomethane or "Tris").

Of course, the present invention is not limited to any particular concentrations of reagents in these solutions and other buffers and detergents can be employed. Nonetheless, in order to achieve high throughput rates, the incorporation reactions and the cleavage reactions are desired to be efficient and accurate. In one embodiment, high reaction rates are achieved by increasing the concentration of reagents, agitation, pH or temperature (or the combination of all these factors). The incorporation rate in addition is dependent on the specific activity and processivity of the polymerase used. In one particular embodiment (which is provided by way of a non-limiting example), the reagents solutions have the following compositions and concentration ranges:
1) Extend A—reversibly terminated labeled (1 nM to 1 uM) and non-labeled nucleotides (1 uM to 100 uM) and a first polymerase (1-500 ug/ml));
2) Extend B—reversibly terminated non-labeled nucleotides (1 uM to 100 uM) and a second polymerase (1-500 ug/ml));
3) Wash solution 1 (50 mM Tris, 50 mM sodium chloride, 1 mM Titriplex III (EDTA), 1 mM methylenediphosphonic acid, 0.05% (w/v)Tween 20, and 0.04% (w/v) ProClin 300);
4) Cleave solution (50-100 mM TCEP);
5) Wash solution 2 (50 mM Tris, 50 mM sodium chloride, 1 mM Titriplex III (EDTA), 1 mM methylenediphosphonic acid, 0.05% (w/v)Tween 20, and 0.04% (w/v) ProClin 300)

In one embodiment, a first polymerase incorporates labeled nucleotides better than a second polymerase, which incorporates unlabeled nucleotides more efficiently. Examples of commercially available polymerases that can be used include, but are not limited to, Therminator I-III. These polymerases are derived from *Thermococcus* sp. and carry mutations allowing for incorporation of modified nucleotides.

In one embodiment, a sequenceable DNA (i.e., for example, DNA that is preferably loaded on the chip or slide) is subjected to these reagents and compositions in the instrument, and the sequencing is performed using an automated protocol (see, Table 1). Again, it is not intended that the present invention be limited to any precise protocol or series of method steps. The order and number of steps can vary, as well as the time taken for each step. By way of a non-limiting example, in one embodiment, the instrument protocol comprises (and is configured) as follows:
1. Extend A—0.5-5 minutes (delivery+agitation)
2. Extend B—1-20 minutes (delivery+agitation)
3. Wash 2—5-10 minutes (10-20.times.delivery and agitation)
4. Image. In one embodiment, the imaging reagant solution (either solution A or B) is as follows:

| | Component | Conc |
|---|---|---|
| Image A | Hepes-Na, pH 7.5, mM | 100 |
| | NaI (mM) | 1 |
| | Glucose oxidase (U/ml) | 5 |
| | EGTA (µM) | 25 |
| | Glycerol (% wt/vol) | 0.25 |
| Image B | Hepes-Na, pH 7.5, mM | 100 |
| | NaCl (mM) | 300 |
| | Glucose (mM) | 100 |
| | Trolox (mM) | 2.4 |

5. Cleave A (or Cleave A and B)—1-5 minutes (delivery+agitation)
6. Wash 1—5-10 minutes (10-20.times.delivery and agitation)
7. Wash 2—5-10 minutes (10-20.times.delivery and agitation)
8. Go to step 1

This series of steps may be repeated as a cycle as many times as desired and images may be taken and subsequently analyzed to decode the DNA sequence present at each location. As noted above, in one embodiment, one or more of these steps is associated with an intrument "station" wherein each station has the requisite reagent and/or wash delivery elements to perform the step. Flow cells are moved from one station to another station in order to carry out the step of the sequencing protocol. Any one of these steps can be done at two stations if desired, i.e. a step taking a longer time can be completed over the course of two stations, each station doing a part (e.g. half of the step).

In one embodiment, a cycle may comprise eight nucleotide analogues including, but not limited to, four nucleotide analogues (e.g., A, T, C, G) that are cleavably labeled and reversibly terminated and/or four nucleotodie analogues (e.g., A, T, G, C) that are unlabeled and reversibly terminated. In one embodiment, the concentration of the labeled nucleotide analogues are at a relatively low concentration. Although it is not necessary to understand the mechanism of an invention, it is believed that the labeled nucleotide analogue concentration is just low enough to be incorporated into a substantial portion of the plurality of primers such that the label is visible and can be detected, with detection being observed whether the primers are detached or self-priming hairpins hybridized to a template DNA. In one embodiment, the unlabeled analogues are at a relatively high concentration. Although it is not necessary to understand the mechanism of an invention, it is believed that the unlabeled analogue high concentration is capable of driving extensions to completion, whether they be detached primers or self-priming hairpins.

Thus, specific compositions and methods of additive to improve sequencing by synthesis performance have been disclosed. It should be apparent, however, to those skilled in the art that many more modifications besides those already described are possible without departing from the inventive concepts herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

I claim:

1. A method of incorporating nucleotides, comprising:
    a) providing i) a plurality of nucleic acid primers and template molecules, ii) an extend reagent comprising polymerase and a plurality of nucleotide analogues, and iii) a wash reagent comprising methylenediphosphonic acid;
    b) hybridizing at least a portion of said primers to at least a portion of said template molecules so as to create hybridized primers;
    c) exposing said hybridized primers to said extend reagent under conditions such that a first nucleotide analogue is incorporated into at least a portion of said hybridized primers so as to create extended primers comprising an incorporated nucleotide analogue;
    d) washing said extended primers with said wash reagent.

2. The method of claim 1, wherein said incorporated nucleotide analogue comprises a label attached through a cleavable disulfide linker to the base.

3. The method of claim 2, wherein said label is fluorescent.

4. The method of claim 2, wherein said extend reagent further comprises cystamine.

5. The method of claim 2, further comprising:
    e) detecting said label of a first labeled nucleotide analogue.

6. The method of claim 5, wherein said detecting of step e) is performed in the presence of methylenediphosphonic acid.

7. The method of claim 1, wherein the concentration of said methylenediphosphonic acid is between 0.1 mM and 4 mM.

8. The method of claim 1, wherein the concentration of said methylenediphosphonic acid is between 0.25 mM and 1 mM.

9. The method of claim 1, wherein the concentration of said methylenediphosphonic acid is between 0.35 mM and 0.65 mM.

* * * * *